United States Patent
Lurquin et al.

(12) 
(10) Patent No.: US 7,612,215 B2
(45) Date of Patent: Nov. 3, 2009

(54) PROCESS FOR PREPARING 2-OXO-1-PYRROLIDINE DERIVATIVES BY INTRAMOLECULAR ALLYLATION

(75) Inventors: Françoise Lurquin, Villers-la-Ville (BE); Frank Driessens, Brussels (BE); Michel Callaert, Brussels (BE)

(73) Assignee: UCB Pharma, S.A., Brussels (BE)

( * ) Notice: Subject to any disclaimer, the term of this patent is extended or adjusted under 35 U.S.C. 154(b) by 192 days.

(21) Appl. No.: 11/570,143

(22) PCT Filed: May 26, 2005

(86) PCT No.: PCT/EP2005/005689

§ 371 (c)(1),
(2), (4) Date: Oct. 12, 2007

(87) PCT Pub. No.: WO2005/121082

PCT Pub. Date: Dec. 22, 2005

(65) Prior Publication Data

US 2008/0125598 A1    May 29, 2008

(30) Foreign Application Priority Data

Jun. 11, 2004 (EP) .................... 04013715

(51) Int. Cl.
*C07D 207/12*  (2006.01)
(52) U.S. Cl. ...................... 548/550; 548/551
(58) Field of Classification Search ................ 548/550, 548/551
See application file for complete search history.

(56) References Cited

FOREIGN PATENT DOCUMENTS

WO      01/62726 A    8/2001

OTHER PUBLICATIONS

Giambastiani et al., "A New Palladium-Catalyzed Intramolecular Allylation to Pyrrolidin-2-Ones", J. Org. Chem., 1998, 804-807, vol. 63.

*Primary Examiner*—Kamal A Saeed
*Assistant Examiner*—Kristin Bianchi
(74) *Attorney, Agent, or Firm*—McDonnell Boehnen Hulbert & Berghoff LLP

(57) ABSTRACT

The present invention relates to a new process for preparing 2-oxo-1-pyrrolidine derivatives of general formula (I), comprising the cyclisation of an intermediate of general formula (II) wherein the substituents are as defined in the specification.

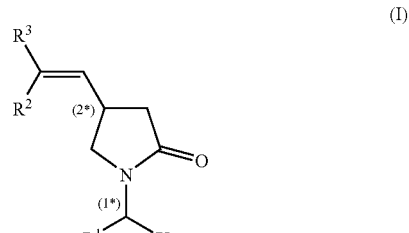

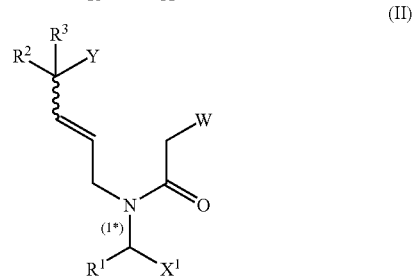

28 Claims, No Drawings

PROCESS FOR PREPARING 2-OXO-1-PYRROLIDINE DERIVATIVES BY INTRAMOLECULAR ALLYLATION

The present invention concerns a process for preparing 2-oxo-1-pyrrolidine derivatives. European Patent No. 0 162 036 B1 discloses the compound (S)-α-ethyl-2-oxo-1-pyrrolidine acetamide, which is known under the International Nonproprietary Name of Levetiracetam.

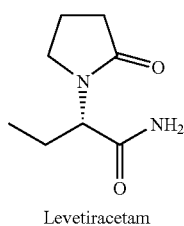

Levetiracetam

Levetiracetam is disclosed as a protective agent for the treatment and prevention of hypoxic and ischemic type aggressions of the central nervous system in EP 0 162 036 B1. This compound is also effective in the treatment of epilepsy.

The preparation of Levetiracetam has been disclosed in European Patent No. 0 162 036 and in British Patent No. 2 225 322.

Other 2-oxo-1-pyrrolidine derivatives and their preparation have been disclosed in WO 01/62726. This patent application specifically describes the synthesis of the two diastereoisomers of (2S)-2-(2-oxo-4-(2,2-difluorovinyl)-1-pyrrolidinyl)butanoic acid 2,2-(dimethyl)ethyl ester. In a first step, 2-amino butyrate is reacted with methyl itaconate. The obtained ester is then transformed into tert-butyl (2S)-2-[4-hydroxymethyl)-2-oxo-1-pyrrolidinyl]butanoate, which is oxidised to an aldehyde in order to react with $CF_2Br_2$ (Wittig reaction).

The present invention relates to another process for the preparation of 2-oxo-1-pyrrolidine derivatives.

The invention provides a process for the preparation of compounds of general formula (I)

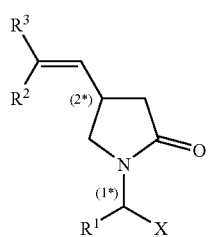

(I)

wherein $R^2$ and $R^3$ are the same or different and each is, independently, hydrogen, $C_{1-4}$ alkyl, cyano, aryl, —COOR$^7$, halogen, $R^8$COO—, $R^9SO_3O$— or $R^{10}SO_2O$—;

$R^1$ is $R^a$, $R^b$, or $C_{2-20}$ alkenyl optionally substituted by aryl;

X is —CONR$^{11}$R$^{12}$, —COOR$^{13}$ or —CN;

$R^7$, $R^8$, $R^9$ and $R^{10}$ are each independently chosen from hydrogen, $R^{a'}$ and $R^{b'}$;

$R^{11}$, $R^{12}$ and $R^{13}$ are the same or different and each is, independently, hydrogen, $C_{1-4}$ alkyl, aryl, arylalkyl, heteroaryl or heterocycloalkyl;

$R^a$ and $R^{a'}$ each independently represent $C_{1-20}$ alkyl or $C_{1-20}$ alkyl substituted by one or more halogen, hydroxy, thiol, amino, nitro, cyano, thiocyanato, carboxy, sulfonic acid, $R^b$, alkylsulfonyl, arylsulfonyl, alkylsulfinyl, arylsulfinyl, alkylthio, arylthio, alkoxy, aryloxy, sulfonamide, acyl, ester, amido, azido, acyloxy, esteroxy and/or amidooxy;

$R^b$ and $R^{b'}$ each independently represent aryl, heterocycloalkyl, heteroaryl or the same substituted by one or more halogen, $R^a$, hydroxy, thiol, amino, nitro, cyano, thiocyanato, carboxy, sulfonic acid, aryl, alkylsulfonyl, arylsulfonyl, alkylsulfinyl, arylsulfinyl, alkylthio, arylthio, alkoxy, aryloxy, sulfonamide, heterocycloalkyl, heteroaryl, acyl, ester, amido, azido, acyloxy, esteroxy and/or amidooxy; comprising the cyclisation of an intermediate of general formula (II)

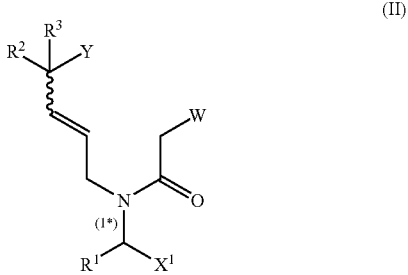

(II)

wherein

Y is a leaving group selected from halogen, —OC(O)R$^{14}$, —OSO$_2$—R$^{15}$ and —OClO$_3$;

$R^{14}$ and $R^{15}$ represent halogen or alkyl, arylalkyl, aryl, each optionally substituted by one or more halogen, alkyl, nitro and/or tertiary amino group;

$X^1$ is as defined for X

W is an electron withdrawing group selected from —COOR$^4$, —COMe, —CN, —PO(OEt)$_2$, —SO$_2$aryl, —COaryl;

$R^4$ represents hydrogen, $C_{1-6}$ alkyl, aryl, arylalkyl, wherein each aryl and arylalkyl may be substituted by one or more halogen, nitro, and/or methoxy;

in the presence of one or more organic and/or inorganic bases.

The term "alkyl", as used herein, represents a saturated monovalent hydrocarbon radicals having straight, branched or cyclic moieties or combinations thereof.

The term "aryl" as used herein, includes an organic radical derived from an aromatic hydrocarbon by removal of one hydrogen, such as phenyl, or naphtyl.

The term "arylalkyl", as used herein, represents an "alkyl" moiety substituted by one or more "aryl" moieties.

The term "alkylaryl", as used herein, represents an "aryl" moiety substituted by one or more "alkyl" moieties.

The term "alkenyl", as used herein, represents branched, unbranched and cyclic hydrocarbon radicals or combinations thereof having at least one double bond.

The term "heterocycloalkyl", as used herein, represents a cyclic alkyl (cycloalkyl) group, having at least one O, S and/or N atom interrupting the carbocyclic ring structure. Preferred heterocycloalkyl are tetrahydrofuranyl, tetrahydropyranyl, piperidinyl, piperazinyl, morpholino and pyrrolidinyl groups.

The term "heteroaryl", as used herein, represents an "aryl" as defined above, having at least one O, S and/or N interrupting the carbocyclic ring structure, such as pyridyl, furyl, pyrrolyl, thienyl, isothiazolyl, imidazolyl, benzimidazolyl, tetrazolyl, pyrazinyl, pyrimnidyl, quinolyl, isoquinolyl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

The term "halogen", as used herein, represents an atom of Cl, Br, F, I.

The term "hydroxy", as used herein, represents a group of formula —OH.

The term "thiol", as used herein, represents a group of formula —SH.

The term "cyano", as used herein, represents a group of formula —CN.

The term "thiocyanato", as used herein, represents a group of formula —SCN.

The term "carboxy", as used herein, represents a group of formula —COOH.

The term "nitro", as used herein, represents a group of formula —$NO_2$.

The term "azido", as used herein, represents a group of formula —$N_3$.

The term "sulfonic acid", as used herein, represents a group of formula —$SO_3H$.

The term "sulfonamide", as used herein, represents a group of formula —$SO_2NH_2$ in which one or both of the hydrogen may optionally be replaced by "alkyl", "aryl", "heteroaryl" and/or "heterocycloalkyl" or the same substituted as defined above.

The term "acyl" as used herein, represents a group of formula $R^cCO$—, wherein $R^c$ represents an "alkyl", "aryl", a "heterocycloalkyl" or "heteroaryl" moiety, or the same substituted as defined above.

The term "ester", as used herein, represents a group of formula —$COOR^d$ wherein $R^d$ represents an "alkyl", "aryl", a "heterocycloalkyl" or "heteroaryl" moiety, or the same substituted as defined above.

The term "alkoxy", as used herein, represents —$OR^e$ groups wherein $R^e$ represents an "alkyl" or a "heterocycloalkyl" moiety, or the same substituted as defined above.

The term "aryloxy", as used herein, represents —$OR^f$ groups wherein $R^f$ represents an "aryl" or a "heteroaryl" moiety, or the same substituted as defined above.

The term "alkylthio" as used herein, represents —$SR^g$ groups wherein $R^g$ represents an "alkyl" or a "heterocycloalkyl" moiety, or the same substituted as defined above.

The term "arylthio", as used herein, represents —$SR^h$ groups wherein $R^h$ represents an "aryl" or a "heteroaryl" moiety, or the same substituted as defined above.

The term "acyloxy", as used herein, represents a group of formula $R^iCOO$—, wherein $R^i$ represents an "alkyl", "aryl", a "heteroaryl" or "heterocycloalkyl" moiety, or the same substituted as defined above.

The term "alkylsulfonyl", as used herein, represents a group of formula —$SO_2R^j$ wherein $R^j$ represents an "alkyl" or a "heterocycloalkyl" moiety, or the same substituted as defined above.

The term "arylsulfonyl", as used herein, represents a group of formula —$SO_2R^k$ wherein $R^k$ represents an "aryl" or a "heteroaryl" moiety, or the same substituted as defined above.

The term "alkylsulfinyl", as used herein, represents a group of formula —SO—$R^l$ wherein $R^l$ represents an "alkyl" or a "heterocycloalkyl" moiety, or the same substituted as defined above.

The term "arylsulfinyl", as used herein, represents a group of formula —SO—$R^m$ wherein $R^m$ represents an "aryl" or a "heteroaryl" moiety, or the same substituted as defined above.

The term "esteroxy", as used herein, represents a group of formula —$OCOOR^n$, wherein $R^n$ represents an "alkyl", "aryl", a "heteroaryl" or "heterocycloalkyl" moiety, or the same substituted as defined above.

The term "amino", as used herein, represents a group of formula —$NH_2$ in which one or both of the hydrogen atoms may optionally be replaced by "alkyl".

The term "amido", as used herein, represents a group of formula —$CONH_2$ in which one or both of the hydrogen atoms may optionally be replaced by "alkyl", "aryl", "heteroaryl" and/or "heterocycloalkyl" or the same substituted as defined above.

The term "amidooxy", as used herein, represents a group of formula —$OCONH_2$ in which one or both of the hydrogen atoms may optionally be replaced by "alkyl", "aryl", "heteroaryl" and/or "heterocycloalkyl" or the same substituted as defined above.

In case more than one substituent $R^a$, $R^{a'}$, $R^b$ or $R^{b'}$ is present in one compound, they can be the same of different.

The term "leaving group", as used herein, has the same meaning by the skilled man (Advanced Organic Chemistry: reactions, mechanisms and structure—Third Edition by Jerry March, John Wiley and Sons Ed.; 1985 page 179) and represents a group which is part of and attached to a substrate molecule; in a reaction where the substrate molecule undergoes a displacement reaction (with for example a nucleophile), the leaving group is then displaced.

Preferred leaving groups, referred to as Y in the present specification, are halogen, —$OC(O)R^{14}$, —$OSO_2$—$C_6H_4$—$CH_3$, —$OSO_2$—$C_6H_4$—Br, —$OSO_2$—$C_6H_4$—$NO_2$, —$OSO_2$—$CH_3$, —$OSO_2$—$CF_3$, —$OSO_2$—$C_4F_9$, —$OSO_2$—$CH_2$—$CF_3$, —$OSO_2$—$(CH_2)_n$—$N+Me_3$, —$OSO_2$—F and —$OClO_3$.

In the process according to the invention, Y is more preferably halogen, most preferably F.

In the process according to the invention, $R^1$ is preferably $C_{1-6}$ alkyl, more preferably methyl, ethyl, n-propyl, isopropyl, n-butyl, or isobutyl; most preferably methyl, ethyl or n-propyl, especially ethyl, $R^2$ and $R^3$ are preferably halogen, more preferably F;

X is preferably —$CONR^{11}R^{12}$, more preferably —$CONH_2$;

W is preferably an electron withdrawing group selected from —$COOR^4$, —CN, —$PO(OEt)_2$; W is more preferably a group of formula —$COOR^4$;

$R^4$ is preferably $C_{1-6}$ alkyl, aryl, arylalkyl, aryl or arylalkyl substituted by one or more halogen, nitro, methoxy; $R^4$ is more preferably $C_{1-6}$ alkyl, most preferably methyl or ethyl.

The cyclisation step is generally conducted in the presence of one or more organic and/or inorganic base.

Preferred organic bases according to the invention are TMG (1,1,3,3-tetramethylguanidine), sparteine, TBD (1,5,7-triazabicyclo(4.4.0)dec-5-ene), BSA (bis(trimethylsilyl)acetamide), DBU (1,8-diazabicyclo[5.4.0]undec-7-ene), BTPP (tert-butylimino-tri(pyrrolidino)phosphorane), DBN (1,5-diazabicyclo(4.3.0)non-5-ene); more preferred is DBU.

Preferred inorganic bases according to the invention are $Na_2CO_3$, $K_2CO_3$, $Cs_2CO_3$, NaH, tert-BuOK, more preferred are $K_2CO_3$ and $CsCO_3$, most preferred is $Cs_2CO_3$.

Inorganic bases can be used alone or in the presence of a phase transfer catalyst. Inorganic bases are preferably used in the presence of a phase transfer catalyst.

Examples of phase transfer catalysts which can be used include, but are not limited to quaternary ammonium salts, such as $BzEt_3NCl$, $Bu_4NHSO_4$, $Bu_4NSO_3BzMe$ and $Bu_4NBr$.

The cyclisation step is generally conducted in the presence of a solvent, preferably an aprotic solvent. Preferred solvents are toluene, tetrahydrofurane, diethoxymethane, dimethylsulfoxyde, ethylacetate, isopropylacetate, methyltertbutylether, dichloromethane, nitriles such as acetonitrile, amides such as dimethylacetamide, N-methylpyrrolidone, dimethylformamide, ketones such as acetone, methylethylketone, methylisobutylketone, or mixtures thereof.

More preferred solvents are polar solvents such as ketones, amides and nitriles, most preferred are methylethylketone, acetonitrile and N-methylpyrrolidone.

The reaction is generally carried out at a temperature of from −40° C. to +80° C., preferably −30° C. to +40° C., more preferably −20° C. to +25° C.

The process according to the invention is also applicable to the preparation of pharmaceutically acceptable salts of compound (I).

The term "pharmaceutically acceptable salts" according to the invention includes therapeutically active, non-toxic base and acid addition salt forms which the compounds of formula (I) are able to form.

The cyclisation of an intermediate of general formula (II) usually results in the formation of an intermediate of formula (VII).

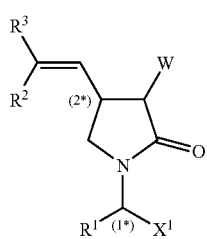

(VII)

In that case, the process additionally comprises the removal of the electron withdrawing group W from compound (VII).

If W is a group of formula —COOR$^{4a}$, especially one wherein R$^{4a}$ is C$_{1-6}$ alkyl, the process according to the invention advantageously contains the decarbalkoxylation of an intermediate of formula (VII a)

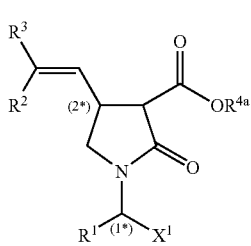

(VII a)

wherein
X$^1$ is as defined above for X;
R$^1$, R$^2$ and R$^3$ are as defined above.
In intermediate of formula (VII a), R$^{4a}$ is preferably methyl or ethyl.

The decarbalkoxylation of intermediate (VII a) can be performed by any method suitable therefore.

The decarbalkoxylation can be performed directly on intermediate (VII a), for example according to the Krapcho decarbalkoxylation method described in A. P. Krapcho et al., *Tetrahedron Letters* 1967, 215, or compound (VII a) is first hydrolysed into the corresponding acid, which is then decarboxylated.

Hence, when W is a group of formula —COOR$^{4a}$ wherein R$^{4a}$ is C$_{1-6}$ alkyl, the process according to the invention more advantageously comprises the hydrolysis of intermediate (VII a).

The hydrolysis of compound of general formula (VII a) is generally performed in the presence of solvent, such as methanol, ethanol, isopropanol, water or mixtures thereof. It is preferably conducted in a mixture of water and methanol.

The hydrolysis is generally conducted in the presence of a base such as K$_2$CO$_3$, Na$_2$CO$_3$, NaOH or LiOH, preferred are K$_2$CO$_3$ and Na$_2$CO$_3$.

In the case where the electron withdrawing group W is or can be transformed to —COOH, especially by hydrolysis of compound (VII a) such as described here above, the process according to the present invention advantageously comprises the decarboxylation of an intermediate of general formula (VII b),

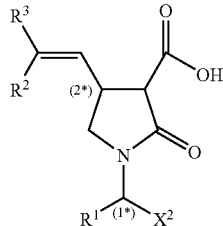

(VII b)

wherein
X$^2$ is as defined above for X;
R$^1$, R$^2$ and R$^3$ are as defined above.

The decarboxylation of intermediate of formula (VII b) is generally performed in the presence of a solvent, preferably in the presence of a solvent having a boiling point superior to 110° C., such as dimethylformamide, dimethylsulfoxide, NMP (N-methyl-2-pyrrolidone), methylisobutylketone, more preferred are methylisobutylketone and NMP.

The decarboxylation is preferably performed at about 130° C. (at normal pressure).

In the process of the present invention, intermediates of formula (II) can be prepared by any method suitable therefore.

Intermediates of formula (II) are preferably prepared by reacting a compound of formula (III)

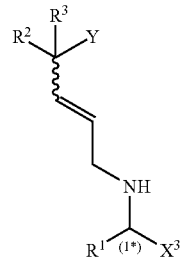

(III)

wherein
X$^3$ is as defined above for X;
Y, R$^1$, R$^2$ and R$^3$ are as defined above,
with a compound of formula (IV)

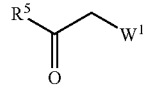

(IV)

wherein W$^1$ is as defined above for W;

$R^5$ is methoxy, ethoxy, chlorine, hydroxy, —ONa or —OK.

In intermediates of formula (III), $X^3$ is preferably —CONR$^{11}$R$^{12}$, more preferably —CONH$_2$.

In compounds of formula (IV), $W^1$ is preferably a group of formula —COOR$^{4b}$, wherein R$^{4b}$ preferably represents C$_{1-6}$ alkyl; more preferably R$^{4b}$ represents a methyl or an ethyl.

In the process of the present invention, intermediates of formula (III) can be prepared by any method suitable therefore, for example by alkylation of a compound of formula (VI) in the presence of a base and/or a catalyst such as Pd.

Intermediates of formula (III) are preferably obtained by reacting a compound of formula (V)

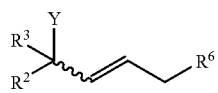

(V)

wherein Y, $R^2$ and $R^3$ are as defined above and $R^6$ is a leaving group such as defined above for Y;

with a compound of formula (VI);

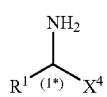

(VI)

wherein $X^4$ is as defined above for X and $R^1$ is as defined above.

In compounds of formula (V), $R^6$ is preferably Cl, Br, I, —OSO$_2$Me, or —OSO$_2$—C$_6$H$_4$—CH$_3$; $R^6$ is more preferably —OSO$_2$—C$_6$H$_4$—CH$_3$.

In the process of the present invention, compounds of formula (V) can be in the form of a Z (Zusammen) or E (Entgegen) isomer, or mixtures thereof.

The process according to the invention relates to the preparation of all stereoisomeric forms such as geometrical and optical enantiomeric and diastereoisomeric forms of the compounds of formula (I) and mixtures (including racemates) thereof.

Compounds of formula (I) have at least two stereogenic centers in their structure which are indicated by (1*) and (2*). These stereogenic centers may be present in a R or S configuration, said R and S notation being used in accordance with the rules described in Pure. Appl. Chem., 45 (1976) 11-30.

The process according to the invention preferably applies to the preparation of compounds of formula (I) wherein the stereogenic center indicated by (1*) is in the (S)- or in the (R)-form; more preferably the stereogenic center indicated by (1*) is in the (S)-form.

The process according to the invention preferably applies to the preparation of compounds of formula (I) wherein the stereogenic center indicated by (2*) is in the (S)- or in the (R)-form; more preferably the stereogenic center indicated by (2*) is in the (S)-form.

The term "(S)-form", as used herein, means that more than 50%, preferably more than 90% of the compounds have the stereogenic carbon atom indicated by an asterisk in the S configuration.

The term "(R)-form", as used herein, means that more than 50%, preferably more than 90% of the compounds have the stereogenic carbon atom indicated by an asterisk in the R configuration.

The process according to the invention preferably applies to the cyclisation of intermediates of general formula (II) wherein the carbon atom indicated by (1*) is in the (S)-form.

It was surprisingly found that no racemisation occurs during the step of cyclisation of intermediate of formula (II) as well as during decarbalkoxylation of intermediate of formula (VII a) or during decarboxylation of intermediate (VII b), and during reaction of compound of formula (III) with compound of formula (IV).

More preferably, the carbon atom indicated by (1*) in compounds of general formula (VI) is in the (S)-form in the process of the present invention.

The process of the invention can optionally contain a step of separation of the different diastereoisomers, particularly a step of separation of one or more of the different diastereoisomers of any of the compounds of formula (I), (VIIa) and (VIIb). The process of the invention preferably contains the separation of the diastereoisomers of intermediate (VII b) by any method suitable therefore, preferably by recristallisation, more preferably in solvents such as acetonitrile, acetone, isopropanol, methanol, water, N-methyl-2 pyrrolidone or mixtures thereof. The process of the invention most preferably comprises a step of isolation of compound of formula (VII b) wherein the carbon atom indicated by (2*) is in the (S)-form.

The process of the present invention can also be used for preparing compounds of general formula (I) in-situ, starting from compounds of general formula (V) and (VI). The term "in-situ" is defined as performing two or more reaction sequences without isolating any of the intermediates that are produced during the reaction sequence.

The present invention particularly applies to the preparation of (2S)-2-[(4S)-4-(2,2-difluorovinyl)-2-oxopyrrolidinyl]butanamide.

The process of the present invention permits to obtain compounds of formula (I) with high purity.

Moreover, the cyclisation step may be performed without the use of toxic or expensive catalyst, especially metal catalysts.

The present invention also relates to synthesis intermediates of formula (II a), (III), (VII a), (VII b) and salts thereof.

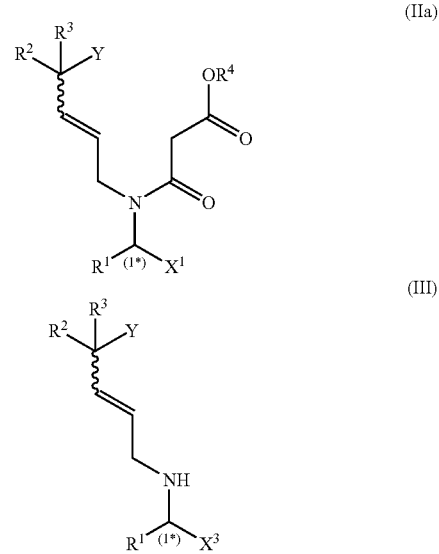

-continued

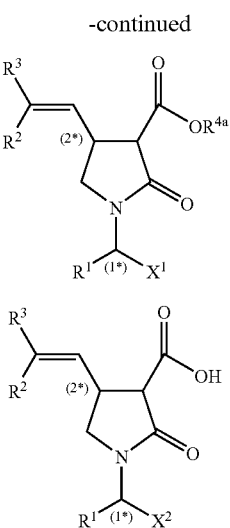

The invention preferably relates to synthesis intermediates of formula (II a), (III), (VII a) and (VII b) wherein $R^1$ is ethyl; $X^1$, $X^2$ and $X^3$ are —$CONH_2$; $R^2$, $R^3$ and Y are F; $R^4$ and $R^{4a}$ is methyl or ethyl.

The invention more preferably relates to intermediates of formula (II a), (III), (VII a) and (VII b) wherein the carbon atom indicated by (1*) is in the (S)-form; most preferably the carbon atom indicated by (2*) in intermediate of general formula (VII b) is in the (S)-form.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLE 1

Preparation of (2S)-2-[(4S)-4-(2,2-difluorovinyl)-2-oxopyrrolidinyl]butanamide 1.1 Synthesis of compound (VI a) (compound of general formula (VI) wherein $X^4$=—$CONH_2$ and $R^1$=ethyl) wherein (1*) is in the (S)-form:

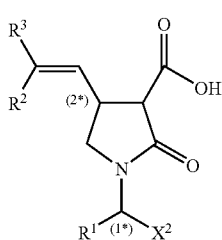

1800 ml L of isopropanol are introduced in a 5 L reactor. 1800 g of (2S)-2-aminobutyramide tartrate are added under stirring at room temperature. 700 ml L of a 25% aqueous solution of ammonium hydroxide are slowly added while maintaining the temperature below 25° C. The mixture is stirred for an additional 3 hours and then the reaction is allowed to complete at 18° C. for 1 hour. The ammonium tartrate is filtered. Yield: 86%.

1.2 Synthesis of compound (V a) (compound of general formula V) wherein $R^2$, $R^3$, Y=F and $R^6$=toluylsulfonyl)

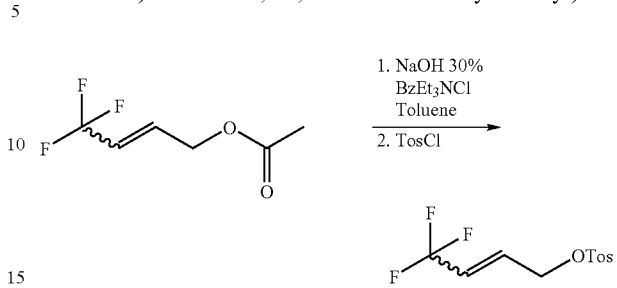

Trifluorobutenol acetate (50 g, 1 eq.), benzyltriethylammonium chloride (5 g, 10% w/w) and toluene (350 ml) are charged in a 1 L double jacket reactor. 130 g of a 30% NaOH solution (2.5 eq.) are added in such a manner that the temperature does not exceed 20° C. The reaction is stirred for 20 hours at this temperature. Tosyl chloride (55.3 g, 0.97 eq.) is added portionwise in 20 minutes and the mixture is stirred at 20° C. for 3 h. Water is then added (150 ml, 3 vol.) and the layers are separated. The organic phase is washed with water (100 ml) and brine (50 ml). The toluene phase is evaporated under vacuum to give 75 g of compound (V a) (Yield: 89%).

1.3 Synthesis of compound (III a) (compound of general formula (III) wherein $R^1$=ethyl; $R^2$, $R^3$, Y=F and $X^3$= —$CONH_2$) wherein (1*) is in the (S)-form:

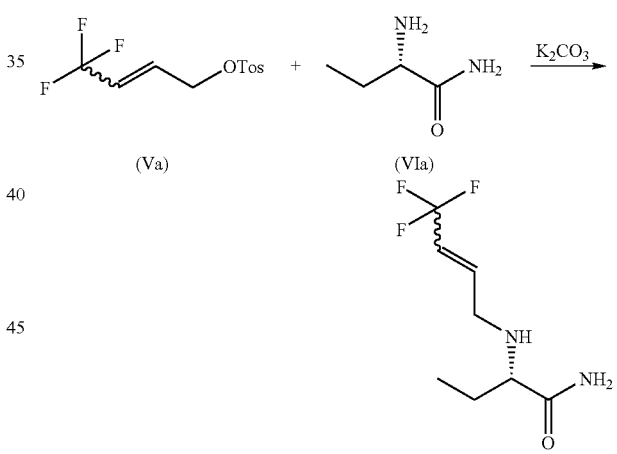

A 1 L three-neck flask with condenser and thermometer is charged with compound (V a) (70 g; 1 eq.), compound (VI a) (30,6 g; 1.2 eq.), $K_2CO_3$ (60,5 g; 2 eq.), isopropanol (210 ml) and isopropyl acetate (210 ml). The mixture is heated to 60° C. and stirred at this temperature for 17 h. The mixture is then cooled to 40° C. and isopropyl acetate (210 ml) is added. The azeotropic mixture of isopropanol and isopropyl acetate (350 ml) is distilled off under vacuum. 210 ml of additional isopropyl acetate are added and 400 ml of azeotropic mixture are further distilled off. Isopropyl acetate (70 ml) is added and the mixture cooled to room temperature. The salts are filtered off and washed with of isopropyl acetate. Water (250 ml) is added and the mixture is cooled to 15° C. 77 ml of 3M hydrochloric acid are added (pH=2). The layers are separated and the aqueous phase is washed with isopropyl acetate. Isopropyl acetate (210 ml) is added and the mixture is cooled to 15° C.

20 ml of a 50% aqueous solution of NaOH is added (pH=7) and then 25 ml of a 10% aqueous solution of Na$_2$CO$_3$ to reach pH=10. After extraction of the aqueous phase with isopropyl acetate and evaporation of the solvent, 37 g of compound (III a) are obtained (Yield: 71%).

Proton NMR (400 MHz, CDCl$_3$): δ=6.75 (s, broad, 1H); 6.43 (dm, J=15.8, 1H); 6.06 (m, 0.1H, cis isomer); 5.85 (m, 1H); 5.71 (m, 0.1H, cis isomer); 5.63 (s, broad, 1H); 3.36 (s, 2H); 3.06 (dd, J=6.8, J=5.6, 1H); 1.79 (m, 1H); 1.68 (m, 1H) 1.45 (s, broad, 1H); 1.00 (t, J=7.7, 3H).

1.4 Synthesis of compound (II b) (compound of general formula (II) wherein W=—COOR$^4$, R$^1$=ethyl; R$^2$, R$^3$, Y=F; R$^4$=methyl and X=—CONH$_2$) wherein (1*) is in the (S)-form:

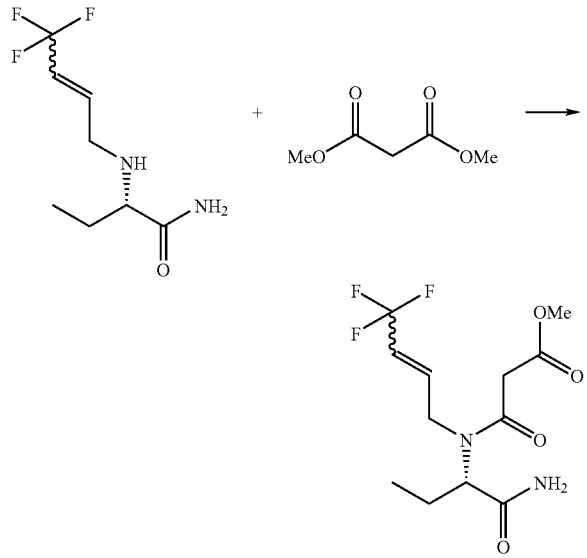

160 g (0.76 mole) of compound (III a) are dissolved in 1005 g (870 ml) of dimethyl malonate at 50° C. in a rotary evaporator. 602 g (520 ml) of dimethyl malonate are charged in a 2 L flask and heated to 110° C. The solution of compound (III a) in dimethyl malonate is added. The mixture is stirred at 110° C. for 40 hours. The dimethyl malonate is then distilled off under vacuum and compound (II b) is used directly in the next step without purification.

1.5 Synthesis of compound of general formula (VII) wherein W=—COOR$^{4a}$, R$^1$=ethyl; R$^2$, R$^3$=F; R$^{4a}$=methyl, X$^1$=—CONH$_2$ and wherein (1*) is in the (S)-form:

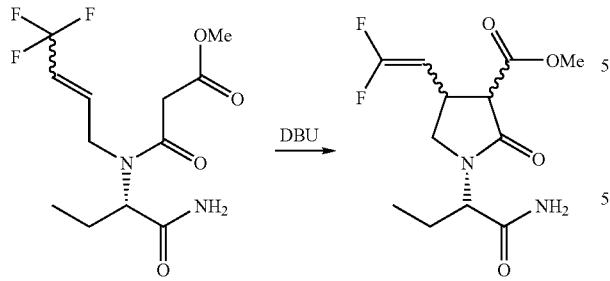

A solution of compound (II b) (304 g) in 607 ml methyl ethyl ketone is slowly added to a solution of diazabicycloundecene (DBU, 179 g) in methyl ethyl ketone (358 ml) under stirring in a 2 L flask at room temperature. After one hour, 300 ml of a 1N solution of HCl are added such that the temperature does not exceed 25° C. (pH=6-7). The layers are separated and the solvent is evaporated. The crude compound is then redissolved in 1520 ml of isopropyl acetate, the organic phase is washed with 100 ml of water and evaporated to give 284 g of the above mentioned compound (Yield: 99%). Proton NMR (400 MHz, CDCl$_3$): δ=6.38 (s, broad, 1H); 5.73 (s, broad, 1H); 4.49 (dd, J=8.9, J=7.0, 1H); 4.27 (ddd, J=24.5, J=9.3, J=1.9, 1H); 3.58 (dd, J=9.6, J=7.7, 1H); 5.02 (m, 2H); 2.68 (dd, J=16.8, J=8.20, 1H); 2.23 (dd, J=16.8, J=8.2, 1H); 1.94 (m, 1H); 1.70 (m, 1H); 0.92 (t, J=7.4, 3H).

1.6 Synthesis of compound (VII b) (compound of general formula (VII) wherein R$^1$=ethyl; R$^2$, R$^3$=F and X$^2$=—CONH$_2$) wherein (1*) and (2*) are in the (S)-form:

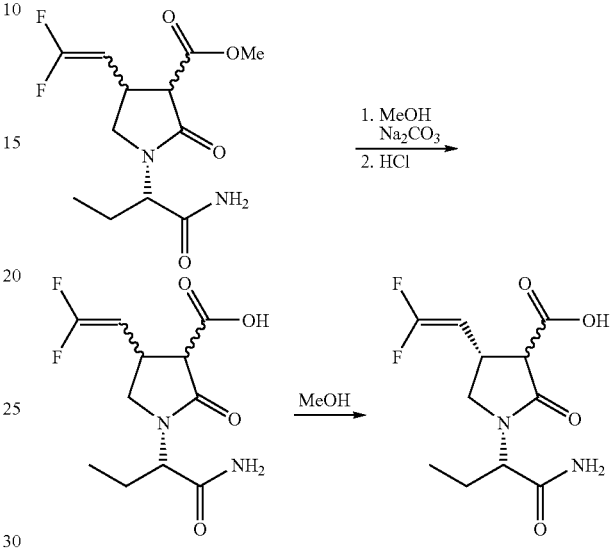

In a 1 L flask, 77.5 g of sodium carbonate are dissolved in 680 ml of water. The mixture is cooled to 20° C. and 85 g of the compound obtained in step 1.5 in solution of methanol is added. The mixture is stirred at 25° C. for 24 h. The aqueous phase is extracted with isopropyl acetate (2×170 ml), and then acidified until pH=2 by addition of 121 ml of concentrated HCl while maintaining the temperature below 25° C. The mixture is then stirred at room temperature for 20 h. The solid thus obtained is filtered, washed with water and then dried under vacuum to give 55 g of crude compound (VII b) (Yield: 68%). After recrystallisation in methanol, pure compound (VII b) is isolated as a white powder (Yield: 70%).

Proton NMR (400 M, DMSO-d$_6$): δ=12.87 (s, broad, 1H); 7.46 (s, 1H); 7.12 (s, 1H); 4.78 (dd, J=26.5, J=7.0, 1H); 4.33 (dd, J=10.6, J=5.20, 1H); 3.53 (t, J=7.0, 1H); 3.28 (m, 3H); 1.81 (m, 1H); 1.61 (m, 1H); 0.79 (t, J=7.3, 3H).

1.7 Synthesis of (2S)-2-[(4S)-4-(2,2-difluorovinyl)-2-oxopyrrolidinyl]butanamide

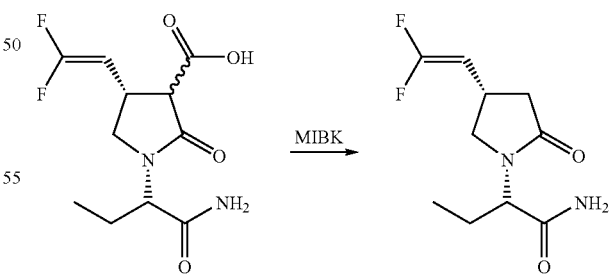

141.9 g of compound (VII b) obtained in step 1.6 and 426 ml of methylisobutylketone are charged in a 1 L flask. The suspension is heated at reflux for 6 h, cooled down to room temperature and then concentrated in vacuo to give the crude (2S)-2-[(4S)-4-(2,2-difluorovinyl)-2-oxopyrrolidinyl]butanamide (127 g) which is recrystallised in methyltertbutylether to afford pure (2S)-2-[(4S)-4-(2,2-difluorovinyl)-2-oxopyrrolidinyl]butanamide (71% yield).

Proton NMR (400 MS, CDCl$_3$): δ=5.68 (s, broad); 6.38 (s, broad) 5.66 (s, broad); 4.58 (dd, J=10.1, J=5.2); 4.48 (dd, J=8.9, J=6.7); 4.28 (ddd, J=24.0, J=9.6, J=1.7); 4.18 (ddd, J=24.0, J=9.1, J=1.6); 3.81 (s); 3.78 (s); 3.66 (dd, J=9.9, J=8.2); 3.60-3.48 (m); 3.48-3.41 (m); 3.36 (d, J=8.5); 3.32-3.22 (m); 2.18 (m); 1.95 (m); 1.87 (s); 1.78-1.58 (m); 0.93 (t, J=7.6).

Alternatively, (2S)-2-[(4S)-4-(2,2-difluorovinyl)-2-oxopyrrolidinyl]butanamide can be treated with charcoal and then isolated by crystallization in a mixture of methylisobutylketone and heptane.

The invention claimed is:

1. A process for the preparation of compounds of general formula (I)

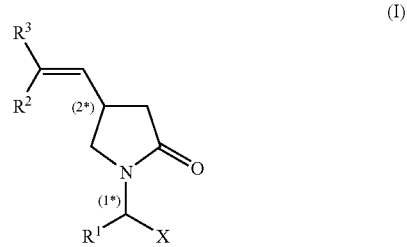

(I)

wherein
  $R^2$ and $R^3$ are the same or different and each is, independently, hydrogen, $C_{1-4}$ alkyl, cyano, aryl, —COOR$^7$, halogen, R$^8$COO—, R$^9$SO$_3$O— or R$^{10}$SO$_2$O—;
  $R^1$ is $R^a$, $R^b$ or $C_{2-20}$ alkenyl optionally substituted by aryl;
  X is —CONR$^{11}$R$^{12}$, —COOR$^{13}$ or —CN;
  $R^7$, $R^8$, $R^9$ and $R^{10}$ are each independently chosen from hydrogen, $R^{a'}$ and $R^{b'}$;
  $R^{11}$, $R^{12}$ and $R^{13}$ are the same or different and each is, independently, hydrogen, $C_{1-4}$ alkyl, aryl, arylalkyl, heteroaryl or heterocycloalkyl;
  $R^a$ and $R^{a'}$ each independently represent $C_{1-20}$ alkyl or $C_{1-20}$ alkyl substituted by one or more halogen, hydroxy, thiol, amino, nitro, cyano, thiocyanato, carboxy, sulfonic acid, $R^b$, alkylsulfonyl, arylsulfonyl, alkylsulfinyl, arylsulfinyl, alkylthio, arylthio, alkoxy, aryloxy, sulfonamide, acyl, ester, amido, azido, acyloxy, esteroxy and/or amidooxy;
  $R^b$ and $R^{b'}$ each independently represent aryl, heterocycloalkyl, heteroaryl or the same substituted by one or more halogen, $R^a$, hydroxy, thiol, amino, nitro, cyano, thiocyanato, carboxy, sulfonic acid, aryl, alkylsulfonyl, arylsulfonyl, alkylsulfinyl, arylsulfinyl, alkylthio, arylthio, alkoxy, aryloxy, sulfonamide, heterocycloalkyl, heteroaryl, acyl, ester, amido, azido, acyloxy, esteroxy and/or amidooxy;
  comprising the cyclisation of an intermediate of general formula (II)

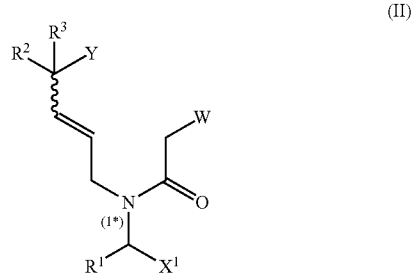

(II)

wherein
  Y is a leaving group selected from halogen, —OC(O)R$^{14}$, —OSO$_2$—R$^{15}$ and —OClO$_3$;
  $R^{14}$ and $R^{15}$ represent halogen or alkyl, arylalkyl, aryl, each optionally substituted by one or more halogen, alkyl, nitro and/or tertiary amino group;
  $X^1$ is as defined for X;
  W is an electron withdrawing group selected from —COOR$^4$, —COMe, —CN, —PO(OEt)$_2$, —SO$_2$aryl, —COaryl;
  $R^4$ represents hydrogen, $C_{1-6}$ alkyl, aryl, arylalkyl, wherein each aryl and arylalkyl may be substituted by one or more halogen, nitro, and/or methoxy;
  in the presence of one or more organic and/or inorganic bases.

2. The process according to claim 1, wherein Y is halogen, —OC(O)R$^{14}$, —OSO$_2$—C$_6$H$_4$—CH$_3$, —OSO$_2$—C$_6$H$_4$—Br, —OSO$_2$—C$_6$H$_4$—NO$_2$, —OSO$_2$—CH$_3$, —OSO$_2$—CF$_3$, —OSO$_2$—C$_4$F$_9$, —OSO$_2$—CH$_2$—CF$_3$, —OSO$_2$—(CH$_2$)$_n$—N$^+$Me$_3$, —OSO$_2$—F or —OClO$_3$.

3. The process according to claim 1, wherein the base is selected from 1,1,3,3-tetramethylguanidine, sparteine, 1,5,7-triazabicyclo(4.4.0)dec-5-ene, bis(trimethylsilyl)acetamide, 1,8-diazabicyclo[5.4.0]undec-7-ene, tert-butylimino-tri(pyrrolidino)phosphorane, 1,5-diazabicyclo(4.3.0)non-5-ene, Na$_2$CO$_3$, K$_2$CO$_3$, Cs$_2$CO$_3$, NaH or tert-BuOK, optionally in the presence of a phase transfer catalyst.

4. The process according to claim 1, comprising the hydrolysis of an intermediate of general formula (VII a)

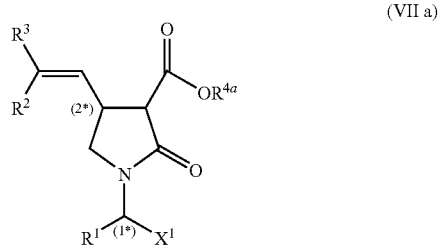

(VII a)

wherein
  $R^{4a}$ is a $C_{1-6}$ alkyl;
  $X^1$ is as defined for X is claim 1;
  $R^1$, $R^2$ and $R^3$ are as defined in claim 1.

5. The process according to claim 1, comprising the decarbalkoxylation of an intermediate of formula (VIIa) as defined in claim 4 or comprising the decarboxylation of an intermediate of general formula (VII b),

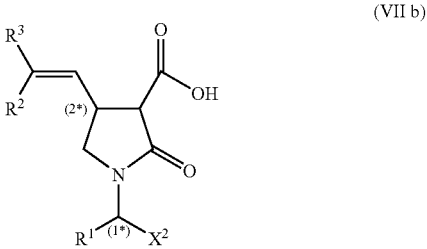

(VII b)

wherein
  $X^2$ is as defined for X in claim 1;
  $R^1$, $R^2$ and $R^3$ are as defined in claim 1.

6. The process according to claim 1, wherein the intermediate of formula (II) is obtained by a method comprising the reaction of an intermediate of formula (III)

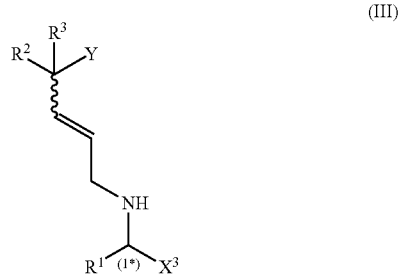
(III)

wherein
$X^3$ is as defined for X in claim 1;
Y, $R^1$, $R^2$ and $R^3$ are as defined in claim 1;
with a compound of formula (IV)

(IV)

wherein
$R^5$ is methoxy, ethoxy, chlorine, hydroxy, —ONa or —OK;
$W^1$ is as defined for W in claim 1.

7. The process according to claim 6, wherein $W^1$ represents a group of formula —COOR$^{4b}$, wherein R$^{4b}$ represents a $C_{1-6}$ alkyl.

8. The process according to claim 6, wherein intermediate (III) is obtained by a method comprising the reaction of a compound of formula (V)

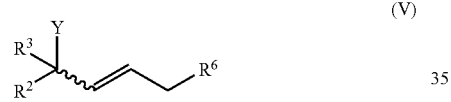
(V)

wherein Y, $R^2$ and $R^3$ are as defined in claim 1 and $R^6$ is a leaving group such as defined for Y in claim 1;
with a compound of formula (VI);

(VI)

wherein $X^4$ is as defined for X in claim 1 and $R^1$ is as defined in claim 1.

9. The process according to claim 8, wherein $R^6$ is —OSO$_2$—C$_6$H$_4$—CH$_3$.

10. The process according to claim 1, comprising a step of separation of one or more of the different diastereoisomers of any of the compounds of formula (I), (VIIa) and (VIIb).

11. The process according to claim 1, wherein the carbon atom indicated by (1*) is in the (S)-form.

12. The process according to claim 1, wherein the carbon atom indicated by (2*) is in the (S)-form.

13. The process according to claim 5, comprising a step of isolation of the compound of formula (VII b) wherein the carbon atom indicated by (2*) is in the (S)-form.

14. The process according to claim 1, wherein W represents a group of formula —COOR$^4$.

15. The process according to claim 14, wherein $R^4$ represents a $C_{1-6}$ alkyl.

16. The process according to claim 1, wherein $R^1$ is a $C_{1-6}$ alkyl.

17. The process according to claim 16, wherein $R^1$ is ethyl.

18. The process according to claim 1, wherein X, $X^1$, $X^2$, $X^3$ and $X^4$ are —CONR$^{11}$R$^{12}$.

19. The process according to claim 18, wherein X, $X^1$, $X^2$, $X^3$ and $X^4$ are —CONH$_2$.

20. The process according to claim 1, wherein $R^2$ and $R^3$ are halogens.

21. The process according to claim 20, wherein $R^2$ and $R^3$ are fluorine.

22. The process according to claim 1, wherein Y is halogen.

23. The process according to claim 22, wherein Y is fluorine.

24. The process according to claim 1, wherein the compound of formula (I) is (2S)-2-[(4S)-4-(2,2-difluorovinyl)-2-oxopyrrolidinyl]butanamide.

25. Synthesis intermediates of formula (II a), (III), (VII a), (VII b) and salts thereof

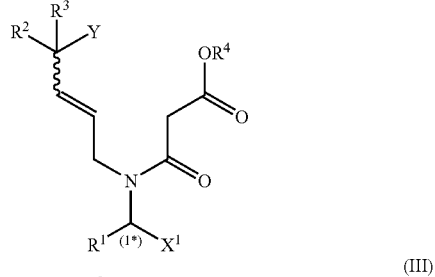
(IIa)

(III)

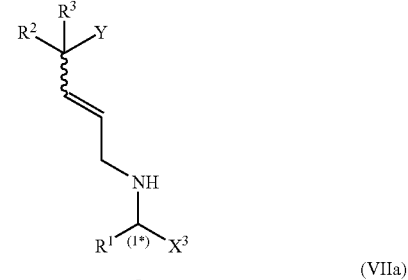
(VIIa)

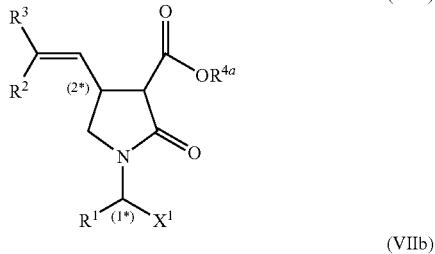
(VIIb)

wherein
$X^1$, $X^2$ and $X^3$ are independently as defined for X in claim 1;
$R^1$, $R^2$, $R^3$, $R^4$ and Y are as defined in claim 1;
and $R^{4a}$ is as defined in claim 4.

26. Synthesis intermediates according to claim 25 wherein $R^1$ is ethyl, $X^1$, $X^2$ and $X^3$ are —CONH$_2$; $R^2$, $R^3$ and Y are F; $R^4$ and $R^{4a}$ are methyl or ethyl.

27. Synthesis intermediates according to claim 25, wherein the carbon atom indicated by (1*) is in the (S)-form.

28. Synthesis intermediate of formula (VII b) according to claim 26, wherein the carbon atom indicated by (2*) is in the (S)-form.

* * * * *